United States Patent
Thiessen et al.

(10) Patent No.: US 11,517,691 B2
(45) Date of Patent: Dec. 6, 2022

(54) METHODS AND SYSTEMS FOR HIGH PRESSURE CONTROLLED VENTILATION

(71) Applicant: Covidien LP, Mansfield, MA (US)

(72) Inventors: Ronald Thiessen, British Columbia (CA); Richard Kauc, Milton (CA)

(73) Assignee: Covidien LP, Mansfield, MA (US)

( * ) Notice: Subject to any disclaimer, the term of this patent is extended or adjusted under 35 U.S.C. 154(b) by 617 days.

(21) Appl. No.: 16/546,523

(22) Filed: Aug. 21, 2019

(65) Prior Publication Data
US 2020/0078547 A1   Mar. 12, 2020

Related U.S. Application Data

(60) Provisional application No. 62/728,336, filed on Sep. 7, 2018.

(51) Int. Cl.
  *A61M 16/00* (2006.01)
  *A61M 16/20* (2006.01)
  *A61M 16/10* (2006.01)

(52) U.S. Cl.
  CPC ...... *A61M 16/024* (2017.08); *A61M 16/0003* (2014.02); *A61M 16/1005* (2014.02); *A61M 16/208* (2013.01); *A61M 2016/0027* (2013.01); *A61M 2205/502* (2013.01); *A61M 2205/52* (2013.01); *A61M 2230/42* (2013.01); *A61M 2230/46* (2013.01)

(58) Field of Classification Search
  CPC .............. A61M 16/024; A61M 16/003; A61M 16/1005; A61M 2230/46; A61M 16/0063; A61M 16/0051
  See application file for complete search history.

(56) References Cited

U.S. PATENT DOCUMENTS

| | | | |
|---|---|---|---|
| 4,127,123 A | 11/1978 | Bird | |
| 4,448,192 A | 5/1984 | Stawitcke et al. | |
| 4,527,557 A | 7/1985 | DeVries et al. | |
| 4,637,385 A | 1/1987 | Rusz | |
| 4,655,213 A | 4/1987 | Rapoport et al. | |
| 4,773,411 A | 9/1988 | Downs | |
| 4,805,612 A | 2/1989 | Jensen | |
| 4,805,613 A | 2/1989 | Bird | |
| 4,821,709 A | 4/1989 | Jensen | |
| 4,986,268 A | 1/1991 | Tehrani | |

(Continued)

FOREIGN PATENT DOCUMENTS

| | | |
|---|---|---|
| EP | 982043 | 3/2000 |
| EP | 1491227 | 12/2004 |

(Continued)

OTHER PUBLICATIONS

PCT International Search Report and Written Opinion in International Application PCT/US2019/049192, dated Dec. 5, 2019, 19 pages.

(Continued)

*Primary Examiner* — Margaret M Luarca (57) ABSTRACT

This disclosure describes systems and methods for providing a high pressure controlled proportional assist ventilation breath type during ventilation of a patient. The disclosure describes a novel breath type that reduces ventilator support (or a percent support setting) based on the occurrence of a predetermined number of high pressure alarms.

20 Claims, 4 Drawing Sheets

(56) References Cited

U.S. PATENT DOCUMENTS

| | | |
|---|---|---|
| 5,044,362 A | 9/1991 | Younes |
| 5,107,830 A | 4/1992 | Younes |
| 5,148,802 A | 9/1992 | Sanders et al. |
| 5,150,291 A | 9/1992 | Cummings et al. |
| 5,161,525 A | 11/1992 | Kimm et al. |
| 5,165,398 A | 11/1992 | Bird |
| 5,237,987 A | 8/1993 | Anderson et al. |
| 5,239,995 A | 8/1993 | Estes et al. |
| 5,271,389 A | 12/1993 | Isaza et al. |
| 5,307,795 A | 5/1994 | Whitwam et al. |
| 5,313,937 A | 5/1994 | Zdrojkowski |
| 5,319,540 A | 6/1994 | Isaza et al. |
| 5,353,788 A | 10/1994 | Miles |
| 5,390,666 A | 2/1995 | Kimm et al. |
| 5,398,676 A | 3/1995 | Press et al. |
| 5,433,193 A | 7/1995 | Sanders et al. |
| 5,438,980 A | 8/1995 | Phillips |
| 5,452,714 A | 9/1995 | Anderson et al. |
| 5,492,113 A | 2/1996 | Estes et al. |
| 5,507,282 A | 4/1996 | Younes |
| 5,513,631 A | 5/1996 | McWilliams |
| RE35,295 E | 7/1996 | Estes et al. |
| 5,535,738 A | 7/1996 | Estes et al. |
| 5,540,222 A | 7/1996 | Younes |
| 5,551,418 A | 9/1996 | Estes et al. |
| 5,572,993 A | 11/1996 | Kurome et al. |
| 5,582,163 A | 12/1996 | Bonassa |
| 5,598,838 A | 2/1997 | Servidio et al. |
| 5,630,411 A | 5/1997 | Holscher |
| 5,632,269 A | 5/1997 | Zdrojkowski |
| 5,660,171 A | 8/1997 | Kimm et al. |
| 5,692,497 A | 12/1997 | Schnitzer et al. |
| 5,694,923 A | 12/1997 | Hete et al. |
| 5,704,345 A | 1/1998 | Berthon-Jones |
| 5,720,278 A | 2/1998 | Lachmann et al. |
| 5,735,267 A | 4/1998 | Tobia |
| 5,743,253 A | 4/1998 | Castor et al. |
| 5,752,506 A | 5/1998 | Richardson |
| 5,765,558 A | 6/1998 | Psaros et al. |
| 5,782,233 A | 7/1998 | Niemi et al. |
| 5,794,615 A | 8/1998 | Estes |
| 5,803,065 A | 9/1998 | Zdrojkowski et al. |
| 5,823,187 A | 10/1998 | Estes et al. |
| 5,868,133 A | 2/1999 | DeVries et al. |
| 5,878,744 A | 3/1999 | Pfeiffer |
| 5,881,717 A | 3/1999 | Isaza |
| 5,884,622 A | 3/1999 | Younes |
| 5,901,704 A | 5/1999 | Estes et al. |
| 5,904,141 A | 5/1999 | Estes et al. |
| 5,927,274 A | 7/1999 | Servidio et al. |
| 5,934,274 A | 8/1999 | Merrick et al. |
| 5,957,130 A | 9/1999 | Krahbichler et al. |
| 5,970,975 A | 10/1999 | Estes et al. |
| 5,975,081 A | 11/1999 | Hood et al. |
| 6,024,089 A | 2/2000 | Wallace et al. |
| 6,029,664 A | 2/2000 | Zdrojkowski et al. |
| 6,029,665 A | 2/2000 | Berthon-Jones |
| 6,041,777 A | 3/2000 | Faithfull et al. |
| 6,105,575 A | 8/2000 | Estes et al. |
| 6,135,105 A | 10/2000 | Lampotang et al. |
| 6,196,222 B1 | 3/2001 | Heinonen et al. |
| 6,209,540 B1 | 4/2001 | Sugiura et al. |
| 6,213,119 B1 | 4/2001 | Brydon et al. |
| 6,240,919 B1 | 6/2001 | MacDonald et al. |
| 6,253,765 B1 | 7/2001 | Hognelid et al. |
| 6,257,234 B1 | 7/2001 | Sun |
| 6,302,105 B1 | 10/2001 | Wickham et al. |
| 6,302,851 B1 | 10/2001 | Gedeon |
| 6,305,372 B1 | 10/2001 | Servidio |
| 6,305,374 B1 | 10/2001 | Zdrojkowski et al. |
| 6,345,619 B1 | 2/2002 | Finn |
| 6,360,745 B1 | 3/2002 | Wallace et al. |
| 6,371,113 B1 | 4/2002 | Tobia et al. |
| 6,427,689 B1 | 8/2002 | Estes et al. |
| 6,431,169 B1 | 8/2002 | do Val et al. |
| 6,439,229 B1 | 8/2002 | Du et al. |
| 6,467,477 B1 | 10/2002 | Frank et al. |
| 6,484,719 B1 | 11/2002 | Berthon-Jones |
| 6,526,970 B2 | 3/2003 | DeVries et al. |
| 6,532,956 B2 | 3/2003 | Hill |
| 6,532,957 B2 | 3/2003 | Berthon-Jones |
| 6,539,940 B2 | 4/2003 | Zdrojkowski et al. |
| 6,553,992 B1 | 4/2003 | Berthon-Jones et al. |
| 6,557,553 B1 | 5/2003 | Borrello |
| 6,557,554 B1 | 5/2003 | Sugiura |
| 6,575,163 B1 | 6/2003 | Berthon-Jones |
| 6,578,575 B1 | 6/2003 | Jonson |
| 6,581,597 B2 | 6/2003 | Sugiura |
| 6,588,422 B1 | 7/2003 | Berthon-Jones et al. |
| 6,595,213 B2 | 7/2003 | Bennarsten |
| 6,609,517 B1 | 8/2003 | Estes et al. |
| 6,612,995 B2 | 9/2003 | Leonhardt et al. |
| 6,622,726 B1 | 9/2003 | Du |
| 6,626,175 B2 | 9/2003 | Jafari et al. |
| 6,629,527 B1 | 10/2003 | Estes et al. |
| 6,629,934 B2 | 10/2003 | Mault et al. |
| 6,631,716 B1 | 10/2003 | Robinson et al. |
| 6,640,806 B2 | 11/2003 | Yurko |
| 6,651,657 B1 | 11/2003 | Manigel et al. |
| 6,668,824 B1 | 12/2003 | Isaza et al. |
| 6,672,300 B1 | 1/2004 | Grant |
| 6,675,797 B1 | 1/2004 | Berthon-Jones |
| 6,679,258 B1 | 1/2004 | Strom |
| 6,688,307 B2 | 2/2004 | Berthon-Jones |
| 6,708,691 B1 | 3/2004 | Hayek |
| 6,755,193 B2 | 6/2004 | Berthon-Jones et al. |
| 6,758,217 B1 | 7/2004 | Younes |
| 6,796,305 B1 | 9/2004 | Banner et al. |
| 6,810,876 B2 | 11/2004 | Berthon-Jones |
| 6,820,613 B2 | 11/2004 | Wenkebach |
| 6,823,866 B2 | 11/2004 | Jafari et al. |
| 6,837,242 B2 | 1/2005 | Younes |
| 6,837,244 B2 | 1/2005 | Yagi et al. |
| 6,854,462 B2 | 2/2005 | Berthon-Jones et al. |
| 6,860,858 B2 | 3/2005 | Green et al. |
| 6,877,511 B2 | 4/2005 | DeVries et al. |
| 6,899,103 B1 | 5/2005 | Hood et al. |
| 6,910,480 B1 | 6/2005 | Berthon-Jones |
| 6,915,803 B2 | 7/2005 | Berthon-Jones et al. |
| 6,920,878 B2 | 7/2005 | Sinderby et al. |
| 6,932,084 B2 | 8/2005 | Estes et al. |
| 6,948,497 B2 | 9/2005 | Zdrojkowski et al. |
| 6,976,487 B1 | 12/2005 | Melker et al. |
| 6,997,881 B2 | 2/2006 | Green et al. |
| 7,000,610 B2 | 2/2006 | Bennarsten et al. |
| 7,000,612 B2 | 2/2006 | Jafari et al. |
| 7,013,892 B2 | 3/2006 | Estes et al. |
| 7,021,310 B1 | 4/2006 | Sinderby et al. |
| 7,032,589 B2 | 4/2006 | Kerechanin, II et al. |
| 7,040,321 B2 | 5/2006 | Göbel |
| 7,055,522 B2 | 6/2006 | Berthon-Jones |
| 7,066,173 B2 | 6/2006 | Banner et al. |
| RE39,225 E | 8/2006 | Isaza et al. |
| 7,096,866 B2 | 8/2006 | Be'eri et al. |
| 7,100,607 B2 | 9/2006 | Zdrojkowski et al. |
| 7,100,609 B2 | 9/2006 | Berthon-Jones et al. |
| 7,137,389 B2 | 11/2006 | Berthon-Jones |
| 7,152,598 B2 | 12/2006 | Morris et al. |
| 7,162,296 B2 | 1/2007 | Leonhardt et al. |
| 7,210,478 B2 | 5/2007 | Banner et al. |
| 7,225,013 B2 | 5/2007 | Geva et al. |
| 7,246,618 B2 | 7/2007 | Habashi |
| 7,255,103 B2 | 8/2007 | Bassin |
| 7,267,121 B2 | 9/2007 | Ivri |
| 7,270,128 B2 | 9/2007 | Berthon-Jones et al. |
| 7,296,573 B2 | 11/2007 | Estes et al. |
| 7,305,987 B2 | 12/2007 | Schöller et al. |
| 7,305,988 B2 | 12/2007 | Acker |
| 7,320,320 B2 | 1/2008 | Berthon-Jones |
| 7,334,578 B2 | 2/2008 | Biondi et al. |
| 7,367,337 B2 | 5/2008 | Berthon-Jones et al. |
| RE40,402 E | 6/2008 | Leonhardt et al. |
| 7,425,201 B2 | 9/2008 | Euliano |
| 7,455,717 B2 | 11/2008 | Sprinkle |

(56) References Cited

U.S. PATENT DOCUMENTS

| | | |
|---|---|---|
| 7,475,685 B2 | 1/2009 | Dietz et al. |
| 7,484,508 B2 | 2/2009 | Younes |
| 7,509,957 B2 | 3/2009 | Duquette et al. |
| 7,516,742 B2 | 4/2009 | Stenzler et al. |
| 7,520,279 B2 | 4/2009 | Berthon-Jones |
| 7,533,670 B1 | 5/2009 | Freitag et al. |
| 7,556,038 B2 | 7/2009 | Kirby et al. |
| 7,588,031 B2 | 9/2009 | Truschel et al. |
| 7,588,543 B2 | 9/2009 | Euliano |
| 7,610,914 B2 | 11/2009 | Bolam et al. |
| 7,617,824 B2 | 11/2009 | Doyle |
| 7,621,270 B2 | 11/2009 | Morris et al. |
| 7,621,271 B2 | 11/2009 | Brugnoli |
| 7,644,713 B2 | 1/2010 | Berthon-Jones |
| 7,672,720 B2 | 3/2010 | Heath |
| 7,678,058 B2 | 3/2010 | Patangay et al. |
| 7,678,061 B2 | 3/2010 | Lee et al. |
| 7,682,312 B2 | 3/2010 | Lurie |
| 7,690,378 B1 | 4/2010 | Turcott |
| 7,697,990 B2 | 4/2010 | Ujhazy et al. |
| 7,708,016 B2 | 5/2010 | Zaiser et al. |
| 7,717,110 B2 | 5/2010 | Kane et al. |
| 7,717,111 B2 | 5/2010 | Schneider et al. |
| 7,722,546 B2 | 5/2010 | Madaus et al. |
| 7,727,160 B2 | 6/2010 | Green et al. |
| 7,730,886 B2 | 6/2010 | Berthon-Jones |
| 7,751,894 B1 | 7/2010 | Freeberg |
| 7,763,097 B2 | 7/2010 | Federspiel et al. |
| 7,770,578 B2 | 8/2010 | Estes et al. |
| 7,793,659 B2 | 9/2010 | Breen |
| 7,802,571 B2 | 9/2010 | Tehrani |
| 7,810,496 B2 | 10/2010 | Estes et al. |
| 7,810,497 B2 | 10/2010 | Pittman et al. |
| 7,819,815 B2 | 10/2010 | Younes |
| 7,841,343 B2 | 11/2010 | Deane |
| 7,849,854 B2 | 12/2010 | DeVries et al. |
| 7,866,318 B2 | 1/2011 | Bassin |
| 7,874,293 B2 | 1/2011 | Gunaratnam et al. |
| 7,914,459 B2 | 3/2011 | Green et al. |
| 7,934,499 B2 | 5/2011 | Berthon-Jones |
| 8,015,974 B2 | 9/2011 | Christopher |
| 8,122,885 B2 | 2/2012 | Berthon-Jones |
| 8,136,521 B2 | 3/2012 | Matthews |
| 8,353,844 B2 | 1/2013 | Jin |
| 8,603,006 B2 | 12/2013 | Mulqueeny |
| 8,617,083 B2 | 12/2013 | Euliano |
| 8,646,447 B2 | 2/2014 | Martin |
| 8,672,858 B2 | 3/2014 | Euliano |
| 8,876,728 B2 | 11/2014 | Welzien |
| 8,910,632 B2 | 12/2014 | Tiedje |
| 8,920,333 B2 | 12/2014 | Younes |
| 8,950,399 B2 | 2/2015 | Handzsuj |
| 9,220,856 B2 | 12/2015 | Martin |
| 9,392,964 B2 | 7/2016 | Mulqueeny |
| 9,592,356 B2 | 3/2017 | Truschel |
| 9,839,760 B2 | 12/2017 | Bonassa |
| 9,895,083 B2 | 2/2018 | Zheng |
| 9,980,943 B2 | 5/2018 | Burkin |
| 10,022,084 B2 | 7/2018 | Nonaka |
| 10,165,966 B2 | 1/2019 | Banner |
| 10,207,068 B2 | 2/2019 | Jafari |
| 10,293,126 B2 | 5/2019 | Berry |
| 2003/0010339 A1 | 1/2003 | Banner |
| 2006/0155336 A1 | 7/2006 | Heath |
| 2006/0174884 A1 | 8/2006 | Habashi |
| 2006/0235324 A1 | 10/2006 | Lynn |
| 2006/0249148 A1 | 11/2006 | Younes |
| 2006/0278223 A1 | 12/2006 | Younes |
| 2007/0000494 A1 | 1/2007 | Banner et al. |
| 2007/0028921 A1 | 2/2007 | Banner et al. |
| 2007/0044796 A1 | 3/2007 | Zdrojkowski et al. |
| 2007/0044799 A1 | 3/2007 | Hete et al. |
| 2007/0215146 A1 | 9/2007 | Douglas et al. |
| 2007/0272241 A1 | 11/2007 | Sanborn et al. |
| 2008/0011301 A1 | 1/2008 | Qian |
| 2008/0017198 A1 | 1/2008 | Ivri |
| 2008/0045813 A1 | 2/2008 | Phuah et al. |
| 2008/0053441 A1 | 3/2008 | Gottlib et al. |
| 2008/0053443 A1 | 3/2008 | Estes et al. |
| 2008/0053444 A1 | 3/2008 | Estes et al. |
| 2008/0072901 A1 | 3/2008 | Habashi |
| 2008/0110461 A1 | 5/2008 | Mulqueeny et al. |
| 2008/0142012 A1 | 6/2008 | Farnsworth et al. |
| 2008/0163872 A1 | 7/2008 | Negele et al. |
| 2008/0185002 A1 | 8/2008 | Berthon-Jones et al. |
| 2008/0196720 A1 | 8/2008 | Kollmeyer et al. |
| 2008/0202528 A1 | 8/2008 | Carter et al. |
| 2008/0216832 A1 | 9/2008 | Carter et al. |
| 2008/0216833 A1 | 9/2008 | Pujol et al. |
| 2008/0234595 A1 | 9/2008 | Ranieri et al. |
| 2008/0257349 A1 | 10/2008 | Hedner et al. |
| 2008/0283061 A1 | 11/2008 | Tiedje |
| 2008/0295839 A1 | 12/2008 | Habashi |
| 2009/0020120 A1 | 1/2009 | Schatzl et al. |
| 2009/0038616 A1 | 2/2009 | Mulcahy et al. |
| 2009/0056719 A1 | 3/2009 | Newman, Jr. |
| 2009/0084381 A1 | 4/2009 | DeVries et al. |
| 2009/0095298 A1 | 4/2009 | Gunaratnam et al. |
| 2009/0107502 A1 | 4/2009 | Younes |
| 2009/0114224 A1 | 5/2009 | Handzsuj et al. |
| 2009/0159082 A1 | 6/2009 | Eger |
| 2009/0173347 A1 | 7/2009 | Berthon-Jones |
| 2009/0188502 A1 | 7/2009 | Tiedje |
| 2009/0199855 A1 | 8/2009 | Davenport |
| 2009/0221926 A1 | 9/2009 | Younes |
| 2009/0229611 A1 | 9/2009 | Martin et al. |
| 2009/0241951 A1 | 10/2009 | Jafari et al. |
| 2009/0241955 A1 | 10/2009 | Jafari et al. |
| 2010/0051029 A1 | 3/2010 | Jafari et al. |
| 2010/0065055 A1 | 3/2010 | Morris et al. |
| 2010/0065057 A1 | 3/2010 | Berthon-Jones |
| 2010/0069761 A1 | 3/2010 | Karst et al. |
| 2010/0071696 A1 | 3/2010 | Jafari |
| 2010/0137380 A1 | 6/2010 | Maybaum |
| 2010/0137723 A1 | 6/2010 | Patangay et al. |
| 2010/0137729 A1 | 6/2010 | Pierry et al. |
| 2010/0137730 A1 | 6/2010 | Hatlestad |
| 2010/0145201 A1 | 6/2010 | Westbrook et al. |
| 2010/0147303 A1 | 6/2010 | Jafari et al. |
| 2010/0152553 A1 | 6/2010 | Ujhazy et al. |
| 2010/0152560 A1 | 6/2010 | Turcott |
| 2010/0170512 A1 | 7/2010 | Kuypers et al. |
| 2010/0174200 A1 | 7/2010 | Wood et al. |
| 2010/0174207 A1 | 7/2010 | Lee et al. |
| 2010/0180898 A1 | 7/2010 | Schneider et al. |
| 2010/0186741 A1 | 7/2010 | Aylsworth et al. |
| 2010/0186742 A1 | 7/2010 | Sherman et al. |
| 2010/0186743 A1 | 7/2010 | Kane et al. |
| 2010/0186744 A1 | 7/2010 | Andrieux |
| 2010/0191076 A1 | 7/2010 | Lewicke et al. |
| 2010/0191137 A1 | 7/2010 | Brada et al. |
| 2010/0192094 A1 | 7/2010 | Jeha et al. |
| 2010/0198086 A1 | 8/2010 | Kuo et al. |
| 2010/0199991 A1 | 8/2010 | Koledin |
| 2010/0210924 A1 | 8/2010 | Parthasarathy et al. |
| 2010/0218764 A1 | 9/2010 | Kwok et al. |
| 2010/0218767 A1 | 9/2010 | Jafari et al. |
| 2010/0218773 A1 | 9/2010 | Thornton |
| 2010/0222692 A1 | 9/2010 | McCawley et al. |
| 2010/0224190 A1 | 9/2010 | Tilley et al. |
| 2010/0228133 A1 | 9/2010 | Averina et al. |
| 2010/0228134 A1 | 9/2010 | Martikka et al. |
| 2010/0229863 A1 | 9/2010 | Enk |
| 2010/0234750 A1 | 9/2010 | Ariav et al. |
| 2010/0236553 A1 | 9/2010 | Jafari et al. |
| 2010/0236554 A1 | 9/2010 | Prete |
| 2010/0236555 A1 | 9/2010 | Jafari et al. |
| 2010/0241009 A1 | 9/2010 | Petkie |
| 2010/0242965 A1 | 9/2010 | Berthon-Jones |
| 2010/0249630 A1 | 9/2010 | Droitcour et al. |
| 2010/0249631 A1 | 9/2010 | Aoki et al. |
| 2010/0249632 A1 | 9/2010 | Lee et al. |
| 2010/0249633 A1 | 9/2010 | Droitcour et al. |
| 2010/0252037 A1 | 10/2010 | Wondka et al. |

(56) References Cited

U.S. PATENT DOCUMENTS

| | | |
|---|---|---|
| 2010/0252039 A1 | 10/2010 | Cipollone et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0252043 A1 | 10/2010 | Freitag |
| 2010/0256463 A1 | 10/2010 | Greenwald et al. |
| 2010/0258116 A1 | 10/2010 | Federspiel et al. |
| 2010/0258124 A1 | 10/2010 | Madaus et al. |
| 2010/0258126 A1 | 10/2010 | Ujhazy et al. |
| 2010/0258127 A1 | 10/2010 | HK |
| 2010/0262032 A1 | 10/2010 | Freeberg |
| 2010/0275920 A1 | 11/2010 | Tham et al. |
| 2010/0288279 A1 | 11/2010 | Seiver et al. |
| 2011/0017214 A1 | 1/2011 | Tehrani |
| 2011/0036352 A1 | 2/2011 | Estes et al. |
| 2011/0041850 A1 | 2/2011 | Vandine et al. |
| 2011/0175728 A1* | 7/2011 | Baker, Jr. ............... G16H 40/63 340/540 |
| 2013/0284172 A1* | 10/2013 | Doyle ............... A61M 16/0051 128/204.23 |
| 2014/0048072 A1 | 2/2014 | Angelico et al. |
| 2015/0068527 A1* | 3/2015 | Cheng ............... A61M 16/0069 128/204.23 |
| 2016/0243324 A1 | 8/2016 | Doyle |
| 2016/0250427 A1 | 9/2016 | Jafari |
| 2016/0256643 A1 | 9/2016 | Graboi |
| 2016/0256656 A1 | 9/2016 | Glenn |
| 2016/0354566 A1 | 12/2016 | Thiessen |
| 2017/0095627 A1 | 4/2017 | Jafari |
| 2017/0164872 A1 | 6/2017 | Sanborn |
| 2017/0182269 A1 | 6/2017 | Masic |
| 2017/0296765 A1 | 10/2017 | Dong |
| 2018/0036500 A1 | 2/2018 | Esmaeil-zadeh-azar |
| 2018/0193578 A1 | 7/2018 | Glenn |
| 2018/0207378 A1 | 7/2018 | Masic |
| 2018/0207379 A1 | 7/2018 | Masic |
| 2018/0325459 A1 | 11/2018 | Nakai |
| 2019/0143058 A1 | 5/2019 | Kimm |

FOREIGN PATENT DOCUMENTS

| | | |
|---|---|---|
| EP | 858352 | 1/2005 |
| EP | 1515767 | 8/2009 |
| WO | WO9014852 | 12/1990 |
| WO | WO 9214505 | 9/1992 |
| WO | WO9308857 | 5/1993 |
| WO | WO199715343 | 5/1997 |
| WO | WO9812965 | 4/1998 |
| WO | WO199951292 | 10/1999 |
| WO | WO199962580 | 12/1999 |
| WO | WO2000/10634 | 3/2000 |
| WO | WO200078380 | 12/2000 |
| WO | WO01/00264 | 1/2001 |
| WO | WO01/00265 | 1/2001 |
| WO | WO200174430 | 10/2001 |
| WO | WO2002028460 | 4/2002 |
| WO | WO2002032488 | 4/2002 |
| WO | WO2003008027 | 1/2003 |
| WO | WO04047621 | 6/2004 |
| WO | WO2005004780 | 1/2005 |
| WO | WO2007102866 | 9/2007 |
| WO | WO2007145948 | 12/2007 |

OTHER PUBLICATIONS

7200 Series Ventilator, Options, and Accessories: Operator's Manual. Nellcor Puritan Bennett, Part No. 22300 A, Sep. 1990, pp. 1-196.
7200 Ventilatory System: Addendum/Errata. Nellcor Puritan Bennett, Part No. 4-023576-00, Rev. A, Apr. 1998, pp. 1-32.
800 Operator's and Technical Reference Manual. Series Ventilator System, Nellcor Puritan Bennett, Part No. 4-070088-00, Rev. L, Aug. 2010, pp. 1-476.
840 Operator's and Technical Reference Manual. Ventilator System, Nellcor Puritan Bennett, Part No. 4-075609-00, Rev. G, Oct. 2006, pp. 1-424.
Puritan Bennett 980 Series Ventilator Operator's Manual, Covidien, Jan. 29, 2014, Part. No. 10077893 A Jan. 2014, 506 pages.

* cited by examiner

METHODS AND SYSTEMS FOR HIGH PRESSURE CONTROLLED VENTILATION

CROSS-REFERENCE TO RELATED APPLICATIONS

This application claims the benefit of U.S. Provisional Patent Application Ser. No. 62/738,336, entitled "Methods and Systems for High Pressure Controlled Ventilation," filed on Sep. 7, 2018, the entire disclosure of which is hereby incorporated herein by reference.

Medical ventilator systems have long been used to provide ventilatory and supplemental oxygen support to patients. These ventilators typically comprise a source of pressurized oxygen which is fluidly connected to the patient through a conduit or tubing. As each patient may require a different ventilation strategy, modern ventilators can be customized for the particular needs of an individual patient. For example, several different ventilator modes or settings have been created to provide better ventilation for patients in various different scenarios.

High Pressure Controlled Proportional Assist Ventilation

This disclosure describes systems and methods for providing a proportional assist breath type during ventilation of a patient that adjusts the support provided to the patient (or the percent support setting) in response to one or more high pressure alarms. The disclosure describes a novel breath type (referred to herein as a high pressure controlled proportional assist ventilation breath type) that reduces the occurrence of delivered pressures that reach or exceed the high pressure limit. The features and methods described below that adjust breath delivery to reduce the occurrence of such high delivered pressure can be implemented as a new breath type, or as an adjustment or optional feature made available on an existing breath type.

In an aspect, a method for ventilating a patient with a ventilator is provided. The method includes receiving a desired percent support setting and calculating a first target airway pressure based at least in part on the desired percent support setting. The method further includes delivering the first target airway pressure to the patient and detecting a set number of consecutive high pressure alarms when delivering the first target airway pressure to the patient. In response to detecting the set number of consecutive high pressure alarms, the method includes reducing the desired percent support setting to form a reduced percent support setting and calculating a second target airway pressure based at least in part on the reduced percent support setting. Additionally, the method includes delivering the second target airway pressure to the patient.

In another aspect, a method for ventilating a patient with a ventilator is provided. The method including calculating a first target airway pressure based at least in part on a percent support setting and, in response to detecting a high pressure alarm, delivering a portion of the first target airway pressure to the patient, where delivering the first target airway pressure is truncated in response to detecting the high pressure alarm. Further, in response to detecting the high pressure alarm, the method includes reducing the percent support setting to form a reduced percent support setting and calculating a second target airway pressure based at least in part on the reduced percent support setting. Additionally, the method includes delivering the second target airway pressure to the patient.

In a yet another aspect, a ventilator system is provided. The ventilator system including a pressure generating system adapted to generate a flow of breathing gas and a ventilation tubing system including a patient interface for connecting the pressure generating system to a patient. The ventilator system further including a processor and a memory for storing and encoding computer-executable instructions that, when executed by the at least one processor, cause the ventilator system to perform operations. The operations including calculating a first target airway pressure based on a percent support setting and, in response to detecting a high pressure alarm, reducing the percent support setting to form a reduced percent support setting. The operations further including calculating a second target airway pressure based on the reduced percent support setting and delivering the second target airway pressure to the patient.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of aspects of systems and methods described below and are not meant to limit the scope of the invention in any manner, which scope shall be based on the claims appended hereto.

DETAILED DESCRIPTION

Although the techniques introduced above and discussed in detail below may be implemented for a variety of medical devices, the present disclosure will discuss the implementation of these techniques in the context of a medical ventilator for use in providing ventilation support to a human patient. A person of skill in the art will understand that the technology described in the context of a medical ventilator for human patients could be adapted for use with other systems such as ventilators for non-human patients and other medical gas transport systems.

Medical ventilators are used to provide a breathing gas to a patient who may otherwise be unable to breathe sufficiently. In modern medical facilities, pressurized air and oxygen sources are often available from wall outlets. Accordingly, ventilators may provide pressure regulating valves (or regulators) connected to centralized sources of pressurized air and pressurized oxygen. The regulating valves function to regulate flow so that respiratory gas having a desired concentration of oxygen is supplied to the patient at desired pressures and rates. Ventilators capable of operating independently of external sources of pressurized air are also available.

While operating a ventilator, it is desirable to control the percentage of oxygen in the gas supplied by the ventilator to the patient. Further, as each patient may require a different ventilation strategy, modern ventilators can be customized for the particular needs of an individual patient. For example, several different ventilator breath types have been created to provide better ventilation for patients in various different scenarios.

Effort-based breath types, such as proportional assist (PA) ventilation, dynamically determine the amount of ventilatory support to deliver based on a continuous estimation/calculation of patient effort and respiratory characteristics. The resulting dynamically generated profile is computed in real- or quasi-real-time and used by the ventilator as a set of points for control of applicable parameters.

Initiation and execution of an effort-based breath, such as PA, have two operation prerequisites: (1) detection of an inspiratory trigger; and (2) detection and measurement of an appreciable amount of patient respiratory effort to constitute a sufficient reference above a ventilator's control signal error deadband. Advanced, sophisticated triggering technologies detect initiation of inspiratory efforts efficiently. In ventilation design, patient effort may be represented by the estimated inspiratory muscle pressure (patient effort) and is calculated based on measured patient inspiration flow. Patient effort is utilized to calculate a target airway pressure for the inspiration. The target airway pressure as used herein is the airway pressure measured at the ventilator-patient interface and is calculated on an on-going basis using patient effort according to the equation of motion. In other words, the target airway pressure is the amount of pressure delivered by the ventilator to the patient.

A PA breath type refers to a type of ventilation in which the ventilator acts as an inspiratory amplifier that provides pressure support based on the patient's effort. The degree of amplification (the "percent support setting") during a PA breath type is set by an operator, for example as a percentage based on the patient's effort. In one implementation of a PA breath type, the ventilator may continuously monitor the patient's instantaneous inspiratory flow and instantaneous net lung volume, which are indicators of the patient's inspiratory effort. These signals, together with ongoing estimates of the patient's lung compliance and lung/airway resistance and the Equation of Motion:

Target Airway Pressure$(t)=E_p \int Q_p dt + Q_p R_p -$Patient Effort$(t)$+PEEP, allow the ventilator to estimate/calculate a patient effort and derive therefrom a target airway pressure to provide the support that assists the patient's inspiratory muscles to the degree selected by the operator as the percent support setting. PEEP as utilized herein refers to the positive end expiratory pressure. $Q_p$ is the instantaneous flow inhaled by the patient, and $E_p$ and $R_p$ are the patient's respiratory elastance and resistance, respectively. In this equation the patient effort is inspiratory muscle pressure. The percent support setting (k) input by the operator divides the total work of breathing between the patient and the ventilator as shown in the equations below:

Patient Effort$(t)=(1.0-k)[E_p \int Q_p dt + Q_p R_p]$; and      1)

Target Airway Pressure$(t)=k[E_p \int Q_p dt + Q_p R_p]$+PEEP.      2)

Patient Effort(t) is the amount of pressure provided by the patient at a time t, and Target airway pressure(t) is the amount of pressure provided by the ventilator at the time t, the bracketed term $[E_p \int Q_p dt + Q_p R_p]$ is the sum of flow and volume terms (elastance multiplied by the integral of flow which gives volume, plus resistance multiplied by flow), and k is the percent support setting (percentage of total pressure to be contributed by the ventilator) input by the operator.

During PA breath types, typically the percent support setting is input by the operator of the ventilator and does not vary. Clinicians, typically, do not utilize a percent support setting unless operating a PA breath type. Accordingly, often times, clinicians or ventilator operators are unfamiliar with a percent support setting and need additional training to learn how to use a proportional assist breath type appropriately.

Further, the PA breath type amplifies patient effort based on rapid calculations of the equation of motion. At 50% support setting, the ventilator is responsible for 50% of the work of breathing, ensuring that the patient is responsible for the remaining 50%. At this 1:1 ratio, if the patient makes a 10 cmH$_2$O peak effort, the ventilator will apply a 10 cmH$_2$O support (above PEEP). As another example, at an 80% support setting, the patient is responsible for 20% of the work of breathing. In essence, the ventilator will provide 4 cmH$_2$O support (above PEEP) for every 1 cmH$_2$O effort made by the patient. The higher the percent support setting, the more risk there is of meeting a high pressure limit, which initiates a high pressure alarm, if a patient suddenly (for a variety of clinical reasons) increases their respiratory efforts. If the patient's effort suddenly increases, and the ventilator amplifies that effort at a high ratio, this can increase the probability of activating the High Pressure Limit/Alarm. When a high pressure alarm occurs or a high pressure limit is met, the ventilator truncates the breath (preventing any more breathing gas from being delivered to the patient) or immediately switches to exhalation and issues a notification that the high pressure alarm occurred.

For example, consider a patient on an 80% support setting (i.e., 1:4 ratio of patient effort to ventilator support); and a PEEP of 10 cm H$_2$O with a high pressure limit set at 40 cmH$_2$O. In this example, the maximum pressure above PEEP that a ventilator can supply during a PA breath type without hitting the high pressure limit is 30 cmH$_2$O. If patient makes a 7 cmH$_2$O effort, the target airway pressure would be (7*4)+10=38 cmH$_2$O by the ventilator. This would not violate the high pressure limit. However, if the patient made an 8 cmH$_2$O effort, the target airway pressure delivered by the ventilator during a PA breath type would be (8*4)+10=42 cmH$_2$O. This amount of pressure violates the high pressure limit and would cause a high pressure alarm.

A clinical problem that occurs with the PA breath type is that if a patient is temporarily strained (i.e., post suction), their effort may increase temporarily to the point that a high pressure limit is met. The onset of the high pressure alarm, as discussed above, truncates the breath, further agitating the patient. When this happens, breath truncation can lead to continual increased patient effort and resulting high pressure limiting. The clinical response required to resolve such a situation is to temporarily decrease the percent support setting to a lower value (typically 50%), in order to reduce the overall target airway pressure, so that the combination of patient effort and amplification of that effort (based on % support setting) no longer activates the high pressure alarm, and allow the patient to settle. However, since this clinical response requires a clinician with the expertise to recognize the situation and the solution, and such expertise is not always immediately present at the bedside, there are times when this situation goes on longer than necessary and often the operator merely abandons the PA breath type instead.

Accordingly, the current disclosure describes a high pressure controlled proportional assist (HPC PA) breath type for ventilating a patient. The HPC PA breath type is similar to the PA breath type except that the HPC PA breath type temporarily reduces the amount of support or the percent support setting or the overall calculated target airway pressure in response to the detection of one or more consecutive high pressure alarms. During the HPC PA breath type, the high pressure alarm functions the same as the alarm would in any other breath type. Accordingly, an HPC PA breath type requires minimal training or education for proper use by clinicians and prevents frustration with or abandonment of a suitable ventilation mode. Further, the HPC PA breath type increases patient comfort and ventilator synchrony in response to a detection of a large patient effort when compared to other PA breath types. The temporary reduction (reducing the amount of support or the percent support setting or the overall calculated target airway pressure) can be implemented as a new HPC PA breath type, or as an adjustment or optional feature made available on an existing PA breath type.

As used herein, patient parameters are any parameters determined based on measurements taken of the patient, such as heart rate, respiration rate, a blood oxygen level (SpO2), inspiratory lung flow, expiratory lung flow, airway pressure, and etc. As used herein, ventilator parameters are parameters that are determined by the ventilator and/or are input into the ventilator by an operator, such as a breath type, percent support setting, PEEP, etc. Some parameters may be either ventilator and/or patient parameters depending upon whether or not they are input into the ventilator by an operator or determined by the ventilator.

Figure 1:
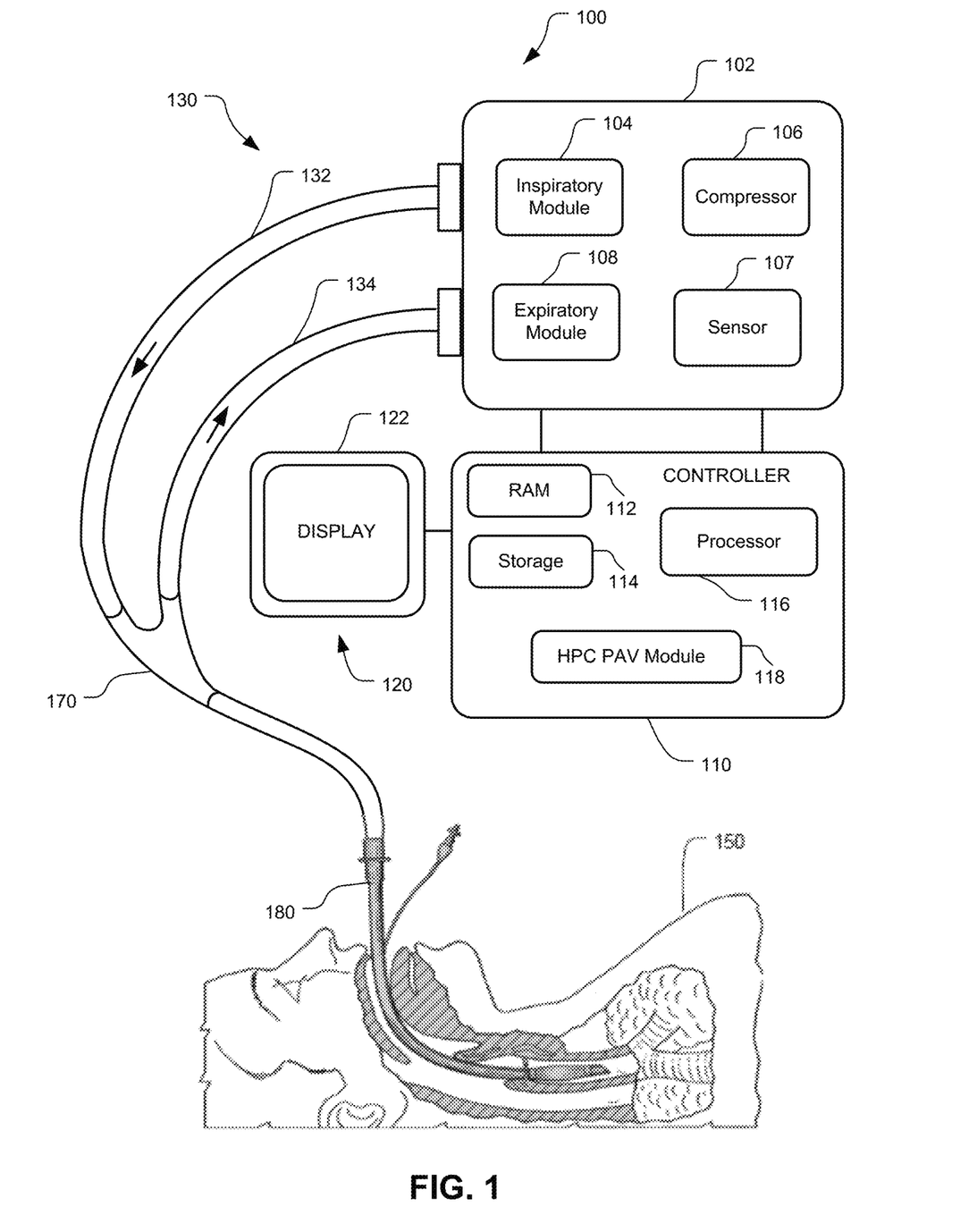
FIG. 1 is schematic diagram illustrating a ventilator ventilating a patient utilizing a high pressure controlled proportional assist ventilation breath type that reduces the occurrence of high pressure alarms, in accordance with aspects of the disclosure.

FIG. 1 is a diagram illustrating an aspect of an exemplary ventilator 100 connected to a human patient 150. Ventilator 100 includes a pneumatic system 102 (also referred to as a pressure generating system 102) for circulating breathing gases to and from patient 150 via the ventilation tubing system 130, which couples the patient 150 to the pneumatic system 102 via an invasive (e.g., endotracheal tube, as shown) or a non-invasive (e.g., nasal mask) patient interface 180.

Ventilation tubing system 130 (or patient circuit 130) may be a two-limb (shown) for carrying gases to and from the patient 150 or a one-limb circuit for carrying gases to the patient. In a two-limb aspect, a fitting, typically referred to as a "wye-fitting" 170, may be provided to couple a patient interface 180 (as shown, an endotracheal tube) to an inspiratory limb 132 and an expiratory limb 134 of the ventilation tubing system 130.

Pneumatic system 102 may be configured in a variety of ways. In the present example, pneumatic system 102 includes an expiratory module 108 coupled with the expiratory limb 134 and an inspiratory module 104 coupled with the inspiratory limb 132. Compressor 106 or other source(s) of pressurized gases (e.g., air, oxygen, and/or helium) is coupled with inspiratory module 104 and the expiratory module 108 to provide a gas source for ventilatory support via inspiratory limb 132.

The inspiratory module 104 is configured to deliver gases to the patient 150 according to prescribed ventilatory settings. In some aspects, inspiratory module 104 is configured to provide ventilation according to various breath types, e.g., via volume-control, pressure-control, HPC PA, or via any other suitable breath types.

The expiratory module 108 is configured to release gases from the patient's lungs according to prescribed ventilatory settings. Specifically, expiratory module 108 is associated with and/or controls an expiratory valve for releasing gases from the patient 150.

The ventilator 100 may also include one or more sensors 107 communicatively coupled to ventilator 100. The sensors 107 may be located in the pneumatic system 102, ventilation tubing system 130, and/or on the patient 150. The aspect of FIG. 1 illustrates a sensor 107 in pneumatic system 102.

Sensors 107 may communicate with various components of ventilator 100, e.g., pneumatic system 102, other sensors 107, processor 116, HPC PA module 118, and any other suitable components and/or modules. A module as used herein refers to memory, one or more processors, storage, and/or other components of the type commonly found in command and control computing devices.

In one aspect, sensors 107 generate output and send this output to pneumatic system 102, other sensors 107, processor 116, HPC PA module 118, and any other suitable components and/or modules. Sensors 107 may employ any suitable sensory or derivative technique for monitoring one or more patient parameters or ventilator parameters associated with the ventilation of a patient 150. Sensors 107 may detect changes in patient parameters indicative of patient triggering, for example. Sensors 107 may be placed in any suitable location, e.g., within the ventilatory circuitry or other devices communicatively coupled to the ventilator 100. Further, sensors 107 may be placed in any suitable internal location, such as, within the ventilatory circuitry or within components or modules of ventilator 100. For example, sensors 107 may be coupled to the inspiratory and/or expiratory modules for detecting changes in, for example, circuit pressure and/or flow. In other examples, sensors 107 may be affixed to the ventilatory tubing or may be embedded in the tubing itself. According to some aspects, sensors 107 may be provided at or near the lungs (or diaphragm) for detecting a pressure in the lungs. Additionally or alternatively, sensors 107 may be affixed or embedded in or near wye-fitting 170 and/or patient interface 180. Indeed, any sensory device useful for monitoring changes in measurable parameters during ventilatory treatment may be employed in accordance with aspects described herein.

As should be appreciated, with reference to the Equation of Motion, ventilatory parameters are highly interrelated and, according to aspects, may be either directly or indirectly monitored. That is, parameters may be directly monitored by one or more sensors 107, as described above, or may be indirectly monitored or estimated/calculated using a model, such as a model derived from the Equation of Motion:

(e.g., Target Airway Pressure$(t) = E_p \int Q_p dt + Q_p R_p -$ Patient Effort$(t) +$ PEEP).

The pneumatic system 102 may include a variety of other components, including mixing modules, valves, tubing, accumulators, filters, etc. Controller 110 is operatively coupled with pneumatic system 102, signal measurement and acquisition systems, and an operator interface 120 that may enable an operator to interact with the ventilator 100 (e.g., change ventilator settings, select operational modes, view monitored parameters, etc.).

In one aspect, the operator interface 120 of the ventilator 100 includes a display 122 communicatively coupled to ventilator 100. Display 122 provides various input screens, for receiving clinician input, and various display screens, for presenting useful information to the clinician. In one aspect, the display 122 is configured to include a graphical user interface (GUI). The GUI may be an interactive display, e.g., a touch-sensitive screen or otherwise, and may provide various windows and elements for receiving input and interface command operations. Alternatively, other suitable means of communication with the ventilator 100 may be provided, for instance by a wheel, keyboard, mouse, or other suitable interactive device. Thus, operator interface 120 may accept commands and input through display 122. Display 122 may also provide useful information in the form of various ventilatory data regarding the physical condition of a patient 150. The useful information may be derived by the ventilator 100, based on data collected by a processor 116, and the useful information may be displayed to the clinician in the form of graphs, wave representations, pie graphs, text, or other suitable forms of graphic display. For example, patient data may be displayed on the GUI and/or display 122. Additionally or alternatively, patient data may be communicated to a remote monitoring system coupled via any suitable means to the ventilator 100. In one aspect, the display 122 may display one or more of a current patient effort, a percent support setting, a reduced percent support setting, an increased percent support setting, a notification of a reduced percent support setting, and a notification of a return to a set or desired percent support setting.

Controller 110 may include memory 112, one or more processors 116, storage 114, and/or other components of the type commonly found in command and control computing devices. Controller 110 may further include an HPC PA module 118 configured to deliver gases to the patient 150 according to prescribed breath types as illustrated in FIG. 1. In alternative aspects, the HPC PA module 118 may be located in other components of the ventilator 100, such as the pressure generating system 102 (also known as the pneumatic system 102).

The memory 112 includes non-transitory, computer-readable storage media that stores and/or encodes software (such as computer executable instruction) that is executed by the processor 116 and which controls the operation of the ventilator 100. In an aspect, the memory 112 includes one or more solid-state storage devices such as flash memory chips. In an alternative aspect, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, other hardware memory, or any other medium which can be used to store the desired information and which can be accessed by the computer.

In some aspects, the inspiratory module 104 receives from a user a selection of a breath type such as an HPC PA breath provided by the HPC PA module 118. In some aspects, The HPC PA module 118 receives a percent support setting from operator input or selection. In other aspects, the HPC PA module 118 determines a percent support setting for the breath type based on operator input or selection and/or based on the occurrence of high pressure alarm. In some aspects, the HPC PA module 118 is part of the controller 110 as illustrated in FIG. 1. In other aspects, the HPC PA module 118 is part of the processor 116, pneumatic system 102, and/or a separate computing device in communication with the ventilator 100.

An HPC PA breath is initiated by detecting an inspiratory trigger, and is executed by determining and commanding target airway pressures to be delivered to the patient 150 during inspiration. In some aspects, a patient trigger is calculated or determined based on a measured or monitored patient inspiration flow and/or pressure. Any suitable type of triggering detection for determining a patient trigger may be utilized by the ventilator 100, such as nasal detection, diaphragm detection, and/or brain signal detection. Further, the ventilator 100 may detect patient triggering via a pressure-monitoring method, a flow-monitoring method, direct or indirect measurement of neuromuscular signals, or any other suitable method. Sensors 107 suitable for this detection may include any suitable sensing device as known by a person of skill in the art for a ventilator.

According to an aspect, a pressure-triggering method may involve the ventilator 100 monitoring the circuit pressure, and detecting a slight drop in circuit pressure. The slight drop in circuit pressure may indicate that, in an effort to inspire, the patient's respiratory muscles are creating a slight negative pressure that in turn generates a pressure gradient between the patient's lungs and the airway opening. The ventilator 100 may interpret the slight drop in circuit pressure as a patient trigger and may consequently initiate inspiration by delivering respiratory gases.

Alternatively, the ventilator 100 may detect a flow-triggered event. Specifically, the ventilator 100 may monitor the circuit flow, as described above. If the ventilator 100 detects a slight drop in the base flow through the exhalation module during exhalation, this may indicate, again, that the patient 150 is attempting to inspire. In this case, the ventilator 100 is detecting a drop in bias flow (or baseline flow) attributable to a slight redirection of gases into the patient's lungs (in response to a slightly negative pressure gradient as discussed above). Bias flow refers to a constant flow existing in the circuit during exhalation that enables the ventilator 100 to detect expiratory flow changes and patient triggering.

The HPC PA module 118 sends instructions for an HPC PA breath type to the inspiratory module 104. A PA breath type refers to a type of ventilation in which the ventilator 100 acts as an inspiratory amplifier that provides pressure support to the patient. The degree of amplification (the "percent support setting") is determined by the HPC PA module 118 based on a set or desired percent support setting, and the percent support setting or the target airway pressure may be temporarily reduced after the occurrence of high pressure alarms. The percent support setting determines how much support is provided by the ventilator 100. For example, if the percent support setting is 30%, then the ventilator provides a total pressure to the patient of which 70% is due to the patient effort (generation of muscle pressure) and the remaining 30% is due to the ventilator work, as estimated from the instantaneous flow or other monitored parameters based on the patient effort model used.

In an aspect, the HPC PA breath type determines a target airway pressure to be delivered by the ventilator, by utilizing the following equation:

$$\text{Target Airway Pressure}(t) = k[E_p \int Q_p dt + Q_p R_p] + \text{PEEP}.$$

The percent support setting (k) is held constant over one breath. Every computational cycle (e.g., 5 milliseconds, 10 milliseconds, etc.), the ventilator calculates a target airway pressure, based on the patient's current effort and the percent support setting received from the HPC PA module 118.

The HPC PA module 118 begins inspiratory assist when a trigger is detected and/or inspiratory patient effort is detected by the HPC PA module 118. However, if the patient ceases triggering inspiration, the assist also ceases. Accordingly, in some aspects, the HPC PA module 118 includes a safety feature that has the ventilator 100 deliver a breath to the patient or switches the breath type to a non-spontaneous breath type if a patient trigger is not detected for a set period of time or based on the occurrence of a set event. This safety feature ensures that if a patient stops triggering, the patient will not stop receiving ventilation by the medical ventilator. This type of safety feature can be called backup or apnea ventilation.

Figure 2:
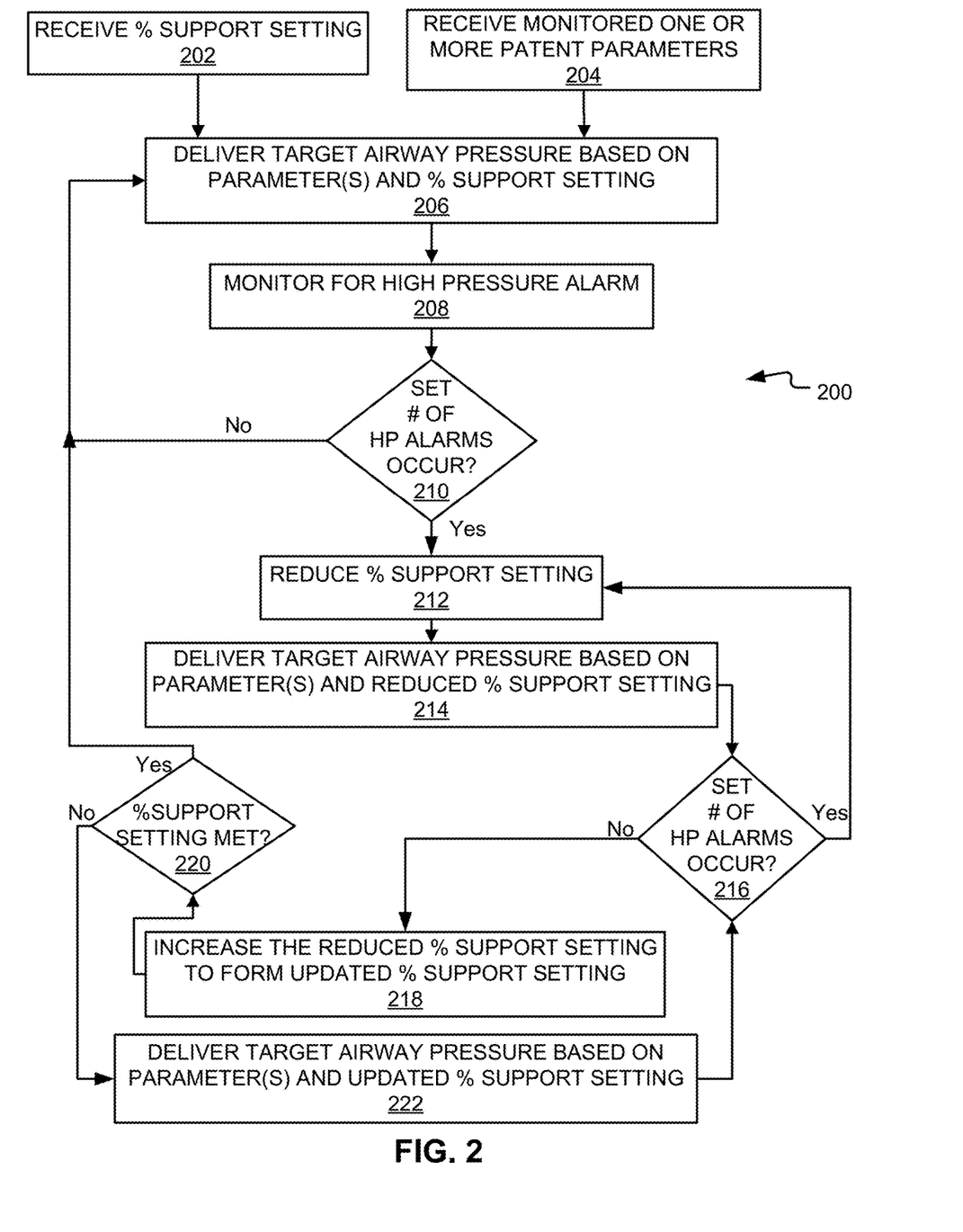
FIG. 2 is a flow diagram illustrating a method for ventilating a patient on a ventilator with a high pressure controlled proportional assist ventilation breath type that reduces the occurrence of high pressure alarms, in accordance with aspects of the disclosure.
Figure 3:
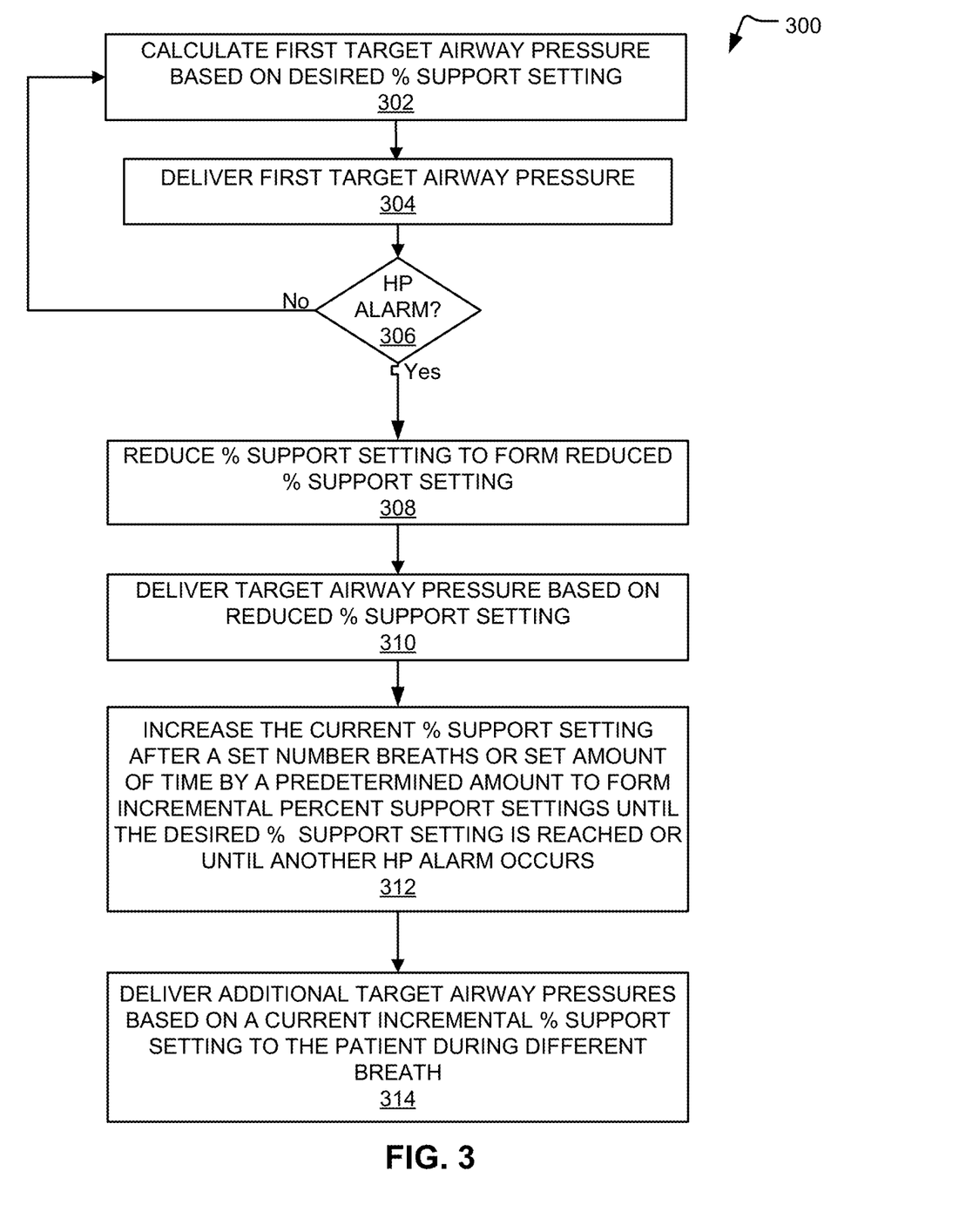
FIG. 3 is a flow diagram illustrating a method for ventilating a patient on a ventilator with a high pressure controlled proportional assist ventilation breath type that reduces the occurrence of high pressure alarms, in accordance with aspects of the disclosure.
Figure 4:
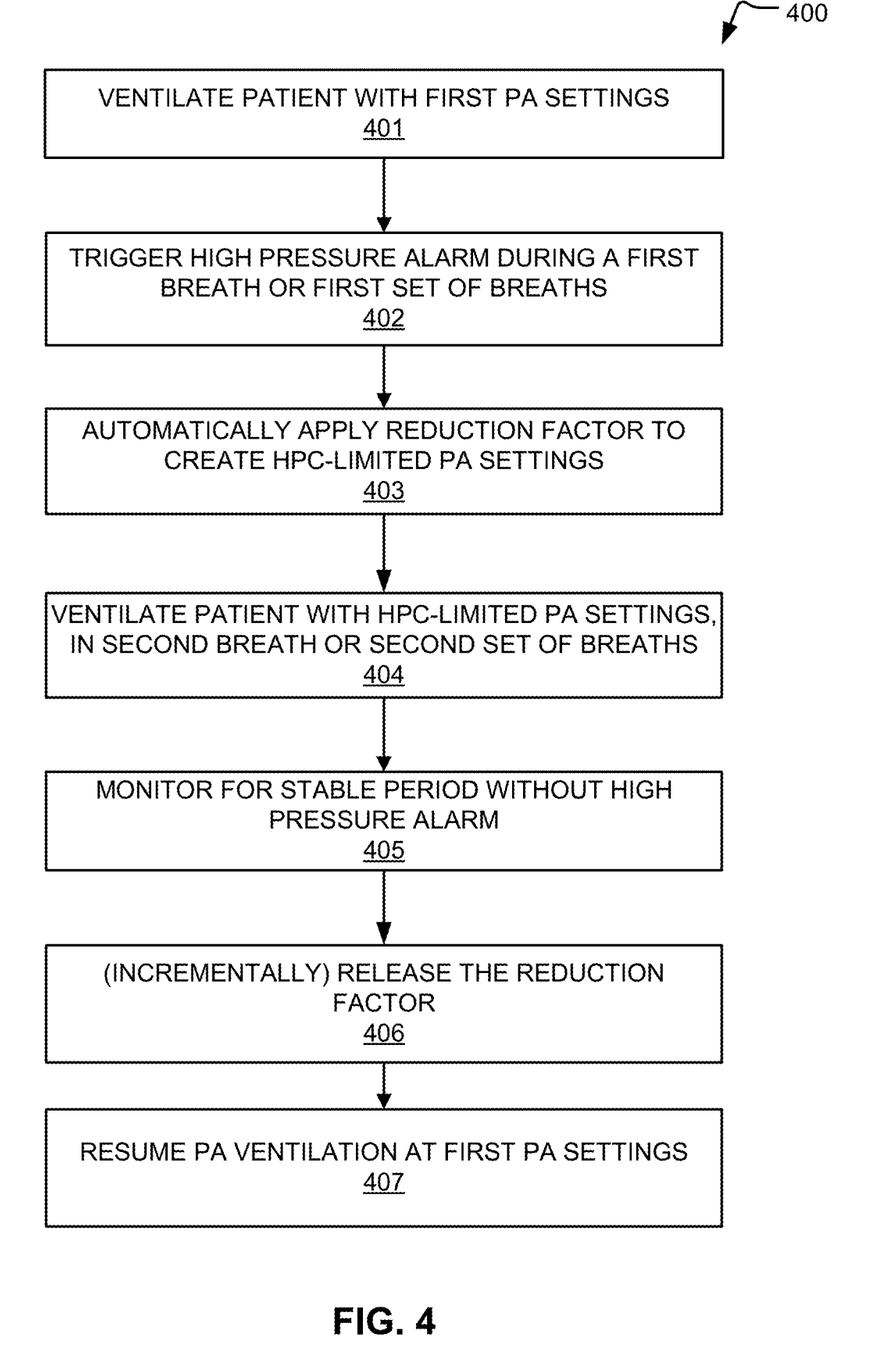
FIG. 4 is a flow diagram illustrating a method for ventilating a patient on a ventilator with a high pressure controlled proportional assist ventilation breath type that reduces the occurrence of high pressure alarms, in accordance with aspects of the disclosure.

The HPC PA module 118 determines the target airway pressure to deliver by utilizing method 200 and/or method 300 and/or method 400 as described below and/or as illustrated in FIGS. 2-4.

FIG. 2 is a flow diagram illustrating a method 200 for ventilating a patient with a ventilator that utilizes a HPC PA breath type, in accordance with aspects of the disclosure. The HPC PA breath type delivers a target airway pressure calculated based on a percent support setting and/or the occurrence of high pressure alarm (or the meeting of a high pressure limit). For example, the HPC PA breath type temporarily adjusts a desired or set percent support setting (the amount of support provided by the ventilator) in response to the detection of one or more high pressure alarms or the meeting of a high pressure limit. As discussed above, adjusting the percent support setting to prevent the occurrence of additional high pressure alarms improves the treatment of a patient on a ventilator, improves clinician use of the HPC PA breath type, and/or improves patient comfort during ventilation when compared to the use of traditional PA breath types that do not adjust the percent support setting in response to the occurrence of a high pressure alarm.

As illustrated, method 200 includes receiving operations 202 and 204. Receiving operations 202 and 204 may be performed in any order, simultaneously and/or at overlapping time.

During the support receiving operation 202, the ventilator retrieves or receives a desired percent support setting. In some aspects, the desired percent support setting is input or selected by the operator. In other aspects, the desired percent support setting is determined or selected by the ventilator based on patient parameters and/or operator input. The percent support setting represents the percentage of the total work of breathing (where total work of breathing includes work of breathing done by the patient and work of breathing done by the ventilator) that the ventilator is responsible for during each breath. In one aspect, the desired percent support setting is from 1% to 95%. In other aspects, the desire percent support setting is 10%, 20%, 25%, 30%, 40%, 50%, 60%, 70%, 75%, 80%, or 90%. These lists are not meant to be limiting. Any suitable percent support setting to improve the health of the patient may be input by the operator and/or utilized/determined by the ventilator.

During the parameter receiving operation 204, the ventilator retrieves and/or receives one or more monitored patient parameters based on one or more sensor measurements or senor outputs. In some aspects, the ventilator during the parameter receiving operation 204 monitors flow and/or pressure. Sensors suitable for this detection may include any suitable sensing device as known by a person of skill in the art for a ventilator, such as an inspiratory flow sensor, inspiratory pressure sensor, an exhalation flow sensor, an exhalation pressure sensor, and/or exhalation auxiliary pressure sensor. In some aspects, the ventilator during the receiving operation 204 monitors patient parameters every computational cycle or control cycle (e.g., 2 milliseconds, 5 milliseconds, 10 milliseconds, etc.). In some aspects, the computational cycle is the amount of time required by the ventilator to determine and/or calculate a patient parameter.

After receiving operations 202 and 204, normal delivery operation 206 is performed by the ventilator during method 200. During normal delivery operation 206, the ventilator determines or calculates the current patient effort. The current patient effort or actual patient effort as used herein represents the amount of effort exerted by the patient over time during the delivered breath. The current patient effort is calculated every control cycle based on the equation of motion and estimated patient parameters. The ventilator estimates patient parameters based on the measurements directly or indirectly related to monitored patient parameters. In some aspects, the estimated patient parameters include lung compliance (inverse of elastance) and/or lung/airway resistance. In further aspects, the estimated lung compliance, lung elastance and/or lung/airway resistance are estimated based on monitored flow and/or the equation of motion. The estimated patient parameters may be estimated by any processor found in the ventilator.

Next, during normal delivery operation 206, the ventilator calculates a target airway pressure. The ventilator during normal delivery operation 206 calculates the target airway pressure based on the one or more monitored patient parameters (or the current patient effort calculated therefrom) and the desired support setting. In some aspects, the target airway pressure is calculated for a point in the ventilation circuit that is proximal to the lung and would best assist the patient's inspiratory muscles to the degree as estimated in the initial percent support setting. In some aspects, the target airway pressure is calculated utilizing the following equation:

$$\text{Target Airway Pressure}(t) = k[E_p \int Q_p dt + Q_p R_p].$$

Once the target airway pressure has been calculated during normal delivery operation 206, the ventilator delivers the target airway pressure to the patient. The target airway pressure is delivered to the patient by the ventilator during operation 206 in response to the detection of the current patient effort or the current demand for new breath.

Method 200 also includes monitor operation 208. At monitor operation 208, the ventilator monitors for the occurrence of a high pressure alarm or the meeting a high pressure limit. While the flow diagram shows the monitor operation 208 being performed after operation 206, the ventilator may perform monitor operation 208 at the same time as or at an overlapping time as performing receiving operations 202 and 204 and as performing normal delivery operation 206.

A high pressure alarm occurs or a high pressure limit is reached if the target airway pressure in the breathing circuit exceeds a set pressure limit, such as 40 cmH$_2$O. In the event that a high pressure alarm occurs or that a high pressure limit is reached by the ventilator during normal delivery operation 206, the ventilator truncates the delivery of the target airway pressure, such that only a portion of the target airway pressure is delivered to the patient. Once the high pressure limit is reached by the ventilator (or once the ventilator delivers the high pressure limit to the patient), the ventilator immediately stops inspiration and begins exhalation to prevent any more pressure from being delivered to the patient during normal delivery operation 206.

Method 200 also includes count decision operation 210. At count decision operation 210, the ventilator determines if a set number of high pressure alarms have occurred in response to the delivering of the target airway pressure based on the monitoring of the high pressure alarms during operation 208. The set number of high pressure alarms may be 1, 2, 3, 4, 5, 6, 7, 8, 9 or 10. In some aspects, the set number of high pressure alarms is 1. In other aspects, the set number of high pressure alarms is 3. This list of alarm counts is not meant to be limiting. Any suitable count of high pressure alarm for lowering the percent support setting may be utilized by the ventilator during count decision operation 210. The count decision is optional, but it can be employed to delay the following steps (to reduce the percent support setting) until a set number of high pressure alarms have been triggered. If the set number is 2 or 3, for example, the ventilator does not reduce the percent support setting the first time the high pressure limit is reached, but instead waits for the second or third limit violation. The operation 210 may count high pressure alarms in consecutive breaths, or in non-consecutive breaths that are within a span (such as a limited time duration or limited number of breaths). For example, if the set number is 3, the operation 210 may look for high pressure alarms in 3 consecutive breaths, or in 3 out of 4 breaths, or in 3 breaths within 30 seconds. These numbers are examples only, and other numbers can be used.

During count decision operation 210, if the ventilator determines that the set number of high pressure alarms has been reached, then the ventilator performs reduction operation 212. In other words, if the set number of high pressure alarms is met during count decision operation 210, the ventilator determines a new percent support setting that is less than the desired percent support setting. During count decision operation 210, if the ventilator determines that the set number of high pressure alarms has not been reached, then the ventilator selects to again perform operation 206. In other words, if the set number of high pressure alarms is not met during count decision operation 210, the ventilator continues to calculate and deliver to the patient a target airway pressure based on the desired percent support setting. As such, the ventilator may deliver a plurality of different target airway pressures to the patient based on the desired percent support setting and the one or more monitored parameters before operation 212 is performed.

Method 200 also includes reduction operation 212. At reduction operation 212, the ventilator reduces the desired percent support setting to form a reduced percent support setting. In some aspects, the desired present support setting is reduced by a set amount or is reduced to a set amount. For example, the desired present support setting may be set to 40%. In this example, regardless of the desired percent support setting (i.e., 90%, 80%, or 75%), the reduced percent support setting will always be 40%. In other aspects, the desired present support setting may be reduced by half (reduced by 50%). In this example, the desired percent support setting will affect the value of the reduced percent support setting. For example, if the desired percent support setting is 90%, the reduced percent support setting will be set to 45% and if the desired percent support setting is 80%, the reduced percent support setting will be set to 40%. These listed reductions are exemplary only and are not meant to be limiting. Any suitable reduction in the percent support setting may be utilized by the ventilator during reduction operation 212.

Next, the ventilator performs reduced delivery operation 214. At reduced delivery operation 214, the ventilator calculates a target airway pressure based on the reduced percent support setting and the one or more patient parameters (or the current patient effort determined therefrom) received from parameter operation 204. In some aspects, the ventilator at reduced delivery operation 214 calculates or determines a patient effort based on one or more received patient parameters, such as estimated patient compliance and flow rate. Further, at reduced delivery operation 214, the ventilator delivers to the patient the target airway pressure calculated based on the reduced percent support setting. The delivery of different target airway pressures may be differentiated from each other by the use of a descriptive term such as, "first", "second", and "third". For example, the ventilator may deliver one or more "first target airway pressures" to the patient during normal delivery operation 206, the ventilator may deliver one or more "second target airway pressures" to the patient during reduced delivery operation 214, and/or the ventilator may deliver one or more "third target airway pressures" to the patient during increased delivery operation 222.

Method 200 also includes high pressure decision operation 216. High pressure decision operation 216 is the same or similar to count decision operation 210, except that it is performed after the reduced delivery operation 214 and/or increased delivery operation 222. At high pressure decision operation 216, the ventilator determines if a set number of high pressure alarms has occurred in response to the delivering of the target airway pressure (that is calculated based on a percent support setting that is less than the desired percent support setting) based on the monitoring of the high pressure alarms during operation 208. The set number of high pressure alarms may be 1, 2, 3, 4, 5, 6, 7, 8, 9 or 10. In some aspects, the set number of high pressure alarms is 1. In other aspects, the set number of high pressure alarms is 3. This list of alarm counts is not meant to be limiting. Any suitable count of high pressure alarm for lowering the percent support setting may be utilized by the ventilator during high pressure decision operation 216. The set number in operation 216 may be the same as or may differ from the set number in operation 210. For example, in one aspect, the set number in operation 216 is lower than the set number in operation 210, so that further reductions in percent support can take place more rapidly.

During high pressure decision operation 216, if the ventilator determines that the set number of high pressure alarms has been reached, then the ventilator selects to perform reduction operation 212. In other words, if the set number of high pressure alarms is met during high pressure decision operation 216, the ventilator further reduces the percent support setting to an amount that is less than the previously reduced percent support setting. This could be reducing to another set percent support amount (such as reducing to 30%) or reducing by another set amount (such a reducing by half again, or by another amount). During high pressure decision operation 216, if the ventilator determines that the set number of high pressure alarms has not been reached, then the ventilator selects to perform increase operation 218. In other words, if the set number of high pressure alarms is not met during high pressure decision operation 216, the ventilator increases percent support setting to the patient until the desired percent support setting is reached.

As illustrated, method 200 also includes increase operation 218. At increase operation 218, the ventilator increases the reduced percent support to form an increased percent support setting. In some aspects, the ventilator during increase operation 218 increases the prior utilized percent support setting by a predetermined amount after a predetermined amount of time or after a predetermined number of breaths until the desired percent support setting is reached at operation 220 or until set amount of high pressure alarms is reached at operation 216. For example, the percent support setting may be increased by 5% every breath or increased by 10% every two breaths. In another example, the ventilator may also increase current percent support setting by 6% every 400 ms. For example, after a first breath, the reduced percent support setting may be increased by an amount (e.g., 5% or 10%) to form a first updated percent support setting; and after a second breath, may be increased by the amount to form a second updated percent support setting; and so on until the reduced percent support setting reaches the desired percent support setting. These example are not meant to be limiting. The ventilator during increase operation 218 may increase the current percent support setting by any suitable amount at any suitable time until the desired percent support setting is reached. The term "current percent support setting" refers to the percent support setting utilized to calculate the last delivered target airway pressure to the patient.

Accordingly, method 200 includes setting decision operation 220. At setting decision operation 220, the ventilator compares the increased percent support setting to the desired percent support setting. If the ventilator determines at setting decision operation 220 that the increased support setting is equal to or greater than the desired percent support setting based on the comparison, the ventilator selects to perform normal delivery operation 206 again, with the desired percent support setting. If the ventilator determines at setting decision operation 220 that the increased support setting is less than the desired percent support setting based on the comparison, the ventilator selects to perform increased delivery operation 222 again.

At increased delivery operation 222 of method 200, the ventilator calculates a target airway pressure based on the increased percent support setting and the one or more patient parameters (or the current patient effort determined therefrom) received from parameter receiving operation 204. As such, in some aspects, the ventilator at increased delivery operation 222 calculates or determines a patient effort based on one or more received patient parameters, such as estimated patient compliance and flow rate. Further, at increased delivery operation 222, the ventilator delivers to the patient the target airway pressure calculated based on the increased percent support setting from operation 218.

After the performance of increased delivery operation 222, the ventilator performs high pressure decision operation 216 again. In the event that a high pressure alarm occurs or that a high pressure limit is reached by the ventilator during the reduced delivery operation 214 or the increased delivery operation 222, the ventilator truncates the delivery of the target airway pressure, such that only a portion of the target airway pressure calculated based on the increased percent support setting or the reduced percent support setting is delivered to the patient. Once the high pressure limit is reached by the ventilator (or the ventilator delivers the high pressure limit to the patient), the ventilator immediately stops inspiration and begins exhalation to prevent any more pressure from being delivered to the patient during the reduced delivery operation 214 or the increased delivery operation 222.

FIG. 3 is a flow diagram illustrating a method 300 for ventilating a patient with a ventilator that utilizes a HPC PA breath type, in accordance with aspects of the disclosure. The HPC PA breath type delivers a target airway pressure calculated based on a percent support setting and/or the occurrence of high pressure alarm. For example, the HPC PA breath type adjusts a desired or set percent support setting in response to the detection of one or more high pressure alarms. As discussed above, adjusting the percent support setting to prevent the occurrence of additional high pressure alarms improves the treatment of a patient on a ventilator, improves clinician use of the HPC PA breath type, and/or improves patient comfort during ventilation when compared to the use of traditional PA breath types that do not adjust the percent support setting or target airway pressure in response to the occurrence of a high pressure alarm.

As illustrated, method 300 includes a normal calculation operation 302, a normal delivery operation 304, an alarm decision operation 306, a reduction operation 308 and a reduction delivery operation 310. In some aspects, method 300 also includes operation 312 and/or operation 314.

At normal calculation operation 302, the ventilator calculates a first target airway pressure based on a desired percent support setting. At normal delivery operation 304, the ventilator delivers the first target airway pressure to the patient. At alarm decision operation 306, the ventilator determines if a high pressure limit has been met or if a high pressure alarm has occurred. At alarm decision operation 306, if the ventilator determines that the high pressure limit has not been met, the ventilator selects to perform normal calculate operation 302 again. At alarm decision operation 306, if the ventilator determines that the high pressure limit has been met, the ventilator selects to perform reduction operation 308. If a high pressure limit has been met, then the ventilator at normal delivery operation 304 only delivers a portion of the first target airway pressure because the first target airway pressure is truncated in response to an occurrence of a high pressure alarm. At reduction operation 308, the ventilator reduces the percent support setting to form a reduced percent support setting. Next, at reduction delivery operation 310, the ventilator calculates a second target airway pressure based on the reduced percent support setting and then delivers the second target airway pressure to the patient in the next subsequent breath.

At optional operation 312, the ventilator increases the reduced percent support setting after each delivered breath by a set amount to form incremental percent support settings until the desired percent support setting is reached or until another high pressure alarm is detected. In some aspects, the amount of increase is 5% or 10% every breath or every two breaths (or other number of breaths). At optional operation 314, the ventilator calculates additional target airway pressures based on the current incremental percent support setting and delivers to the patient the additional target airway pressures during different breaths. When the percent support setting is reached during operation 314 of method 300, the ventilator selects to perform operation 302 and 304 again instead of operation 314.

The ventilator during method 300, performs operation 306 continuously. As such, the ventilator continues to check for high pressure alarms during operations 310 and 314. If a high pressure alarm is detected during operations 310 and 314 during method 300 by the ventilator, the ventilator selects to perform operation 308 again. For example, if another high pressure alarm is detected by the ventilator, the ventilator reduces a current percent support setting to the reduced percent support setting, calculates a third target airway pressure based on the reduced percent support setting, and then delivers the third target airway pressure to the patient.

FIG. 4 is a flow diagram illustrating a method 400 for ventilating a patient with a ventilator that utilizes a HPC PA breath type, in accordance with aspects of the disclosure. The method provides a way to automatically and temporarily reduce the amplification of breath delivered to the patient, to enable the patient to exert additional inspiratory effort during this temporary time period without triggering high pressure alarms that result in truncated breaths. When the patient settles and calms, the method automatically returns to the prior amplification settings.

The method 400 includes ventilating a patient with first PA settings, at 401. This means delivering a proportional assist breath to a patient, with first PA settings such as a first percent support setting, a calculated pressure target (calculated based on patient effort and the first percent support setting), and high pressure alarm limit. The method includes triggering a high pressure alarm during a first breath or first set of breaths, at 402. For example, this operation may occur where a patient makes a large effort, and the ventilator amplifies this effort at a high percent support setting, resulting in a target airway pressure that is at or above the high pressure limit. The method may include identifying this alarm in a single breath, or in a set of breaths (such as in a certain number of consecutive breaths or in a certain number of non-consecutive breaths within a span, as described in more detail in reference to figures above). When this trigger occurs, the method includes automatically applying a reduction factor to create HPC-limited PA settings, at 403. This could include reducing the percent support setting (as described in more detail in reference to figures above) or reducing the calculated target airway pressure. For example, the target airway pressure could be reduced by a factor (such as reduced in half, or by a third) or by an absolute amount (such as by 10 $cmH_2O$, or other value).

The method then includes ventilating the patient with the HPC-limited PA settings, in a second breath or second set of breaths, at 404. At 405, the ventilator monitors for a stable period without additional high pressure alarms, such as a number of consecutive breaths without triggering an alarm. Then, the method includes releasing the reduction factor, at 406. This could include releasing the reduction factor entirely for the next breath, or incrementally releasing it over two or more breaths. Once the reduction factor has been removed, the method includes resuming PA ventilation at the first PA settings, at 407.

The following is an example scenario. For example, at a percent support setting of 80% (1:4 patient to ventilator support ratio) and a PEEP of 10 $cmH_2O$, when the patient makes an effort of 8 $cmH_2O$, the target airway pressure is 42 $cmH_2O$ (8 multiplied by 4, plus 10). If the high pressure limit is 40 $cmH_2O$, then a high pressure alarm or violation is triggered. The ventilator then applies a reduction factor to the target airway pressure in subsequent breath(s). In this example, the ventilator applies a 25% reduction in target airway pressure (or apply only 75% of the calculated target airway pressure at the 80% support setting). If the patient makes the same effort in a subsequent breath, the delivered pressure is only 34 $cmH_2O$ (8 multiplied by 4, multiplied by 75%, plus 10). In another example, the ventilator applies an absolute reduction of 12 $cmH_2O$, and the delivered pressure is 30 $cmH_2O$ (8 multiplied by 4, minus 12, plus 10). In an embodiment, a method for ventilating a spontaneously inspiring patient includes ventilating the patient with a first proportional assist (PA) setting, triggering a high pressure alarm during a first breath or first set of breaths, applying a reduction factor to create an HPC-limited PA setting, ventilating the patient with the HPC-limited PA setting in a second breath or second set of breaths, releasing the reduction factor in a subsequent breath or set of breaths, and resuming ventilation with the first PA setting. In an embodiment, applying the reduction factor includes reducing a percent support setting. In an embodiment, applying the reduction factor includes reducing the calculated target airway pressure. In an embodiment, applying the reduction factor includes reducing an amplification setting.

In some aspects, a microprocessor-based ventilator that accesses a computer-readable medium having computer-executable instructions for performing the method of ventilating a patient with a medical ventilator is disclosed. This method includes repeatedly performing the steps disclosed in method 200 and/or method 300 and/or method 400 above and/or as illustrated in FIGS. 2 and/or 3 and/or 4.

Those skilled in the art will recognize that the methods and systems of the present disclosure may be implemented in many manners and as such are not to be limited by the foregoing exemplary aspects and examples. In other words, functional elements being performed by a single or multiple components, in various combinations of hardware and software or firmware, and individual functions, can be distributed among software applications at either the client or server level or both. In this regard, any number of the features of the different aspects described herein may be combined into single or multiple aspects, and alternate aspects having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software firmware components described herein as would be understood by those skilled in the art now and hereafter.

Numerous other changes may be made which will readily suggest themselves to those skilled in the art and which are encompassed in the spirit of the disclosure and as defined in the appended claims. While various aspects have been described for purposes of this disclosure, various changes and modifications may be made which are well within the scope of the present invention. Numerous other changes may be made which will readily suggest themselves to those skilled in the art and which are encompassed in the spirit of the disclosure and as defined in the appended claims.

What is claimed is:

1. A method for ventilating a patient with a ventilator comprising:
   receiving a desired percent support setting;
   calculating a first target airway pressure based at least in part on the desired percent support setting;
   delivering the first target airway pressure to the patient;
   detecting a set number of consecutive high pressure alarms when delivering the first target airway pressure to the patient;
   in response to detecting the set number of consecutive high pressure alarms, reducing the desired percent support setting to form a reduced percent support setting;
   calculating a second target airway pressure based at least in part on the reduced percent support setting; and
   delivering the second target airway pressure to the patient.

2. The method of claim 1, further comprising:
   in response to detecting a first high pressure alarm, delivering a portion of the first target airway pressure to the patient, wherein delivery of the first target airway pressure is truncated in response to detecting the first high pressure alarm.

3. The method of claim 1, wherein the percent support setting is reduced automatically in response to detecting the set number of consecutive high pressure alarms.

4. The method of claim 1, further comprising:
   in response to delivering the second target airway pressure to the patient for a period of time, increasing the reduced percent support to form an increased percent support setting;
   calculating a third target airway pressure based at least in part on the increased percent support setting; and
   delivering the third target airway pressure to the patient.

5. The method of claim 4, wherein the reduced percent support setting is increased automatically after the period of time.

6. The method of claim 4, further comprising:
   comparing the desired percent support setting to the increased percent support setting;
   based on the comparison, determining that the desired percent support setting is the same as the increased percent support setting;
   calculating a fourth target airway pressure based at least in part on the desired percent support setting; and
   delivering the fourth target airway pressure to the patient.

7. The method of claim 4, further comprising:
   comparing the desired percent support setting to the increased percent support setting;
   based on the comparison, determining that the increased percent support setting is less than the desired percent support setting;
   increasing the increased percent support setting to form an updated percent support setting;
   calculating a fourth target airway pressure based at least in part on the updated percent support setting; and
   delivering the fourth target airway pressure to the patient.

8. The method of claim 7, further comprising:
   comparing the desired percent support setting to the updated percent support setting;
   based on the comparison, determining that the updated percent support setting is less than the desired percent support setting;
   increasing the updated percent support setting to form a second updated percent support setting;
   in response to detecting a high pressure alarm, reducing the second updated percent support setting to the reduced percent support setting;
   calculating a sixth target airway pressure based at least in part on the reduced percent support setting; and
   delivering the sixth target airway pressure to the patient.

9. The method of claim 4, wherein the reduced percent support setting is increased by one of 5% or 10% to form the increased percent support setting.

10. The method of claim 4, wherein the reduced percent support setting is increased after delivering the second target airway pressure to the patient for a predetermined number of breathes.

11. The method of claim 1, wherein the reduced percent support setting is 50%.

12. The method of claim 1, wherein the desired percent support setting is reduced by a predetermine percentage to form the reduced percent support setting.

13. A method for ventilating a patient with a ventilator comprising:
    calculating a first target airway pressure based at least in part on a percent support setting;
    in response to detecting a high pressure alarm, delivering a portion of the first target airway pressure to the patient, wherein delivering the first target airway pressure is truncated in response to detecting the high pressure alarm;
    in response to detecting the high pressure alarm, reducing the percent support setting to form a reduced percent support setting;
    calculating a second target airway pressure based at least in part on the reduced percent support setting; and
    delivering the second target airway pressure to the patient.

14. The method of claim 13, further comprising:
    after each subsequent breath, increasing the reduced percent support setting by a predetermined amount to form a set of incremental percent support settings;
    calculating subsequent target airway pressures based on each of the set of incremental percent support settings; and
    delivering the subsequent target airway pressures to the patient until the percent support setting is reached or a subsequent high pressure alarm is detected.

15. The method of claim 14, further comprising:
    when the percent support setting is reached, calculating a third target airway pressure based on the percent support setting; and
    delivering the third target airway pressure to the patient.

16. The method of claim 14, wherein the predetermined amount is 5%.

17. The method of claim 14, wherein the predetermined amount is 10%.

18. The method of claim 14, further comprising:
    detecting the subsequent high pressure alarm;
    in response to the detecting the subsequent high pressure alarm, reducing the current incremental percent support setting to the reduced percent support setting;
    calculating a third target airway pressure based on the reduced percent support setting; and
    delivering the third target airway pressure to the patient.

19. A ventilator system comprising:
    a pressure generating system adapted to generate a flow of breathing gas;
    a ventilation tubing system including a patient interface for connecting the pressure generating system to a patient;

at least one processor; and a memory for storing and encoding computer-executable instructions that, when executed by the at least one processor, cause the ventilator system to:

calculate a first target airway pressure based on a percent support setting;

in response to detecting a high pressure alarm, reduce the percent support setting to form a reduced percent support setting;

calculate a second target airway pressure based on the reduced percent support setting; and deliver the second target airway pressure to the patient.

20. The ventilator system of claim 19, wherein the computer-executable instructions when executed by the at least one processor further cause the ventilator system to:

after each subsequent breath, increase the reduced percent support setting after each delivered breath by a predetermined amount to form a set of incremental percent support settings;

calculate subsequent target airway pressures based on each of the set of incremental percent support settings; and deliver the subsequent target airway pressures to the patient until the percent support setting is reached or a subsequent high pressure alarm is detected.

* * * * *